United States Patent
Okamoto et al.

(10) Patent No.: US 6,225,492 B1
(45) Date of Patent: May 1, 2001

(54) PURIFICATION METHOD OF CYANATE

(75) Inventors: Satoshi Okamoto, Ibaraki; Hisashi Watabu, Hyogo, both of (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/413,538

(22) Filed: Oct. 6, 1999

(30) Foreign Application Priority Data

Oct. 7, 1998 (JP) .................................................. 10-284868
Nov. 27, 1998 (JP) .................................................. 10-336932

(51) Int. Cl.⁷ .............................................. C07C 255/00
(52) U.S. Cl. ............................................................ 558/389
(58) Field of Search ............................................... 558/389

(56) References Cited

U.S. PATENT DOCUMENTS

| 3,553,244 | 1/1971 | Grigat et al. |
| 4,028,393 | 6/1977 | Rottloff et al. |
| 4,981,994 | 1/1991 | Jackson |
| 5,420,342 | 5/1995 | Craig, Jr. |
| 5,932,762 | 8/1999 | Falchetto et al. |
| 5,942,640 * | 8/1999 | Crevasco et al. |

FOREIGN PATENT DOCUMENTS

| 41-1928 | 2/1941 | (JP) |
| 7-53497 | 2/1995 | (JP) |
| 8-92192 | 4/1996 | (JP) |

* cited by examiner

*Primary Examiner*—Paul J. Killos
*Assistant Examiner*—John N Calve
(74) *Attorney, Agent, or Firm*—Pillsbury Winthrop LLP

(57) ABSTRACT

Provided is a method for purifying a cyanate at high yield from a cyanate crude product solution comprising a cyanate represented by the general formula (1), unsubstituted phenol and non-alcoholic solvent by contacting with a poor solvent containing an alcohol and water, to crystallize the cyanate:

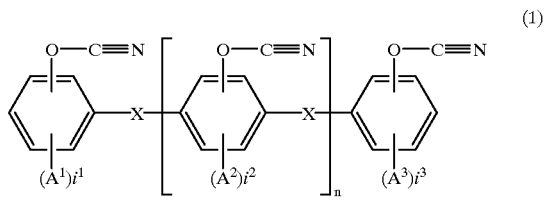

(1)

in the formula (1), $A^1$ to $A^3$ each independently represents a hydrogen atom or an alkyl group having 1 to 6 carbon atoms; X represents a single bond, an organic group having 1 to 20 carbon atoms, a carbonyl group, a sulfone group, a divalent sulfur atom or oxygen atom; n represents an integer of 0 to 3; and $i^1$ to $i^3$ each independently represents an integer of 0 to 4. And also provided is a method for separating alcohol from non-alcoholic solvent effectively.

9 Claims, No Drawings

PURIFICATION METHOD OF CYANATE

BACKGROUND OF THE INVENTION

1. Field of the Invention

The present invention relates to a method for purifying a cyanate, which is useful for a sealant, laminate, composite material, molding material and adhesive of electronic parts, efficiently and at high purity from a cyanate crude product solution containing an unsubstituted phenol.

2. Description of the Related Art

As a method for producing a cyanate industrially, there is a well known method in which a cyanogen halide and a phenol are reacted in the presence of a tertiary aliphatic amine (A. W. Snow in "Chemistry and Technology of Cyanate Ester Resins", Chap. 2 (Ed. T. Hamerton), Blackie Academic and Professional, Glasgow, 1994, pp. 7 to 57). However, a cyanate obtained in this method can not avoid remaining of unreacted phenols and the like. Further, when a cyanate is stored for a long period of time, it is easily hydrolyzed to give a phenol. If such a phenol contained in the cyanate, there occurs a problem that the phenol functions as a polymerization catalyst of cyanate and makes difficult the control of thermo-setting reaction using the cyanate.

As a method for purifying a cyanate in a crude product solution containing an unsubstituted phenol, there is reported a distillation method. However, some cyanates have sublimation property under reduced pressure or polymerization property catalyzed by the unsubstituted phenol as a catalyst when heated, therefore, distillation is not satisfactory method for safely obtaining a cyanate of high purity in high yield.

Also reported is a method in which purification is conducted by crystallizing or precipitating a crude product solution of a cyanate. However, a conventionally suggested method in which crystallization is conducted by cooling using only a good solvent gives low yield, and a conventionally suggested method in which crystallization is conducted by contacting a crude product solution of a cyanate with a poor solvent such as hexane, 2-propanol and the like has a problem that the isolation yield is low since removal of a raw material phenol is difficult and further a part of a cyanate is dissolved in the poor solvent.

Moreover, a filtrate obtained in this operation contains alcohol and non-alcoholic solvent, and disposal thereof is complicated, causing obstruction in efficiency of production of a cyanate itself in practice.

SUMMARY OF THE INVENTION

An object of the present invention is to provide a safe and simple method for purifying a cyanate having high purity at high yield from a cyanate crude product solution containing unsubstituted phenol.

According to the present invention, there is provided a method for purifying a cyanate wherein a cyanate crude product solution comprising a cyanate represented by the general formula (1), unsubstituted phenol and non-alcoholic solvent is allowed to contact with a poor solvent containing an alcohol and water, to crystallize or precipitate said cyanate represented by the general formula (1):

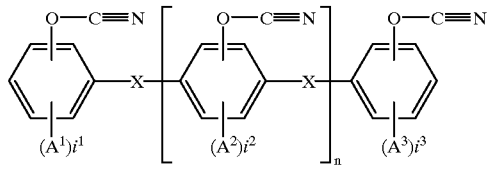

in the formula (1), $A^1$ to $A^3$ each independently represents a hydrogen atom or an alkyl group having 1 to 6 carbon atoms; X represents a single bond, an organic group having 1 to 20 carbon atoms, a carbonyl group, a sulfone group, a divalent sulfur atom or oxygen atom; n represents an integer of 0 to 3; and $i^1$ to $i^3$ each independently represents an integer of 0 to 4.

DETAILED DESCRIPTION OF THE INVENTION

The purification method of the present invention includes a step in which a cyanate crude product solution is allowed to contact with a specific poor solvent to crystallize or precipitate the cyanate.

The cyanate crude product solution used in the present invention comprises a cyanate represented by the above-described general formula (1) as a desired material, and unsubstituted phenols.

The cyanate which is contained in the above-described crude product solution may be any compound providing it satisfies the above-described general formula (1). In the formula, x represents a single bond, an organic group having 1 to 20 carbon atoms, a carbonyl group, a sulfone group, a divalent sulfur atom or oxygen atom. Examples of the organic group having 1 to 20 carbon atoms include linear or branched alkylene groups, such as —$(CH_2)m$—, —$CH((CH_2)mH)$—, —$C((CH_2)mH)_2$— and —$C(CF_3)_2$— (here, m represents an integer of 1 to 20). The symbol n represents preferably an integer of from 0 to 20, and more preferably 0.

Examples of the cyanate include: 4,4'-dicyanatediphenyl, 3,3', 5,5'-tetramethyl-4,4'-dicyanatediphenyl, bis(4-cyanatephenyl)methane, bis(4-cyanate-3-methylphenyl) methane, bis(4-cyanate-3-t-butylphenyl)methane, bis(4-cyanate-3-i-propylphenyl)methane, bis(4-cyanate-3,5-dimethylphenyl)methane, bis(2-cyanate-3-t-butyl-5-methylphenyl)methane, bis(4-cyanatephenyl)ethane, bis(4-cyanate-3-methylphenyl)ethane, bis(4-cyanate-3-t-butylphenyl)ethane, bis(4-cyanate-3-iso-propyphenyl) ethane, bis(4-cyanate- 3,5-dimethylphenyl)ethane, bis(2-cyanate-3-t-butyl-5-methylphenyl)ethane, 2,2-bis(4-cyanatephenyl)propane, 2,2-bis(4-cyanate-3-methylphenyl) propane, 2,2-bis(4-cyanate-3-t-butylphenyl)propane, 2,2-bis (4-cyanate-3-iso-propylphenyl)propane, 2,2-bis(4-cyanate-3,5-dimethylphenyl)propane, 2,2-bis(2-cyanate-3-t-butyl-5-methylphenyl)propane, 2,2-bis(4-cyanate-3-t-butyl-6-methylphenyl)propane, 2,2-bis(3-allyl-4-cyanatephenyl) propane, 1,1-bis(4-cyanatephenyl)butane, 1,1-bis(4-cyanate-3-methylphenyl)butane, 1,1-bis(4-cyanate-3-t-butylphenyl)butane, 1,1-bis(4-cyanate-3-iso-propylphenyl) butane, 1,1-bis(4-cyanate-3,5-dimethylphenyl)butane, 1,1-bis(2-cyanate-3-t-butyl-5-methylphenyl)butane, 1,1-bis(4-cyanate-3-t-butyl-6-methylphenyl)butane, 2,2-bis(3-allyl-4-cyanatephenyl)propane, 1,1-bis(3-allyl-4-cyanatephenyl) butane, 1,1-bis(4-cyanatephenyl)cyclohexane, 1,1-bis(4-cyanate-3-methylphenyl)cyclohexane, bis(4-cyanatephenyl)

sulfide, bis(4-cyanate-3-methylphenyl) sulfide, bis(4-cyanate-3-t-butylphenyl) sulfide, bis(4-cyanate-3-iso-propylphenyl) sulfide, bis(4-cyanate-3,5-dimethylphenyl) sulfide, bis(2-cyanate-3-t-butyl-5-methylphenyl) sulfide, bis(4-cyanatephenyl)sulfone, bis(4-cyanate-3-methylphenyl) sulfone, bis(4-cyanate-3-t-butylphenyl)sulfone, bis(4-cyanate- 3-iso-propylphenyl)sulfone, bis(4-cyanate-3,5-dimethylphenyl)sulfone, bis(2-cyanate-3-t-butyl-5-methylphenyl)sulfone, bis(4-cyanatephenyl) ether, bis(4-cyanate-3-methylphenyl) ether, bis(4-cyanate-3-t-butylphenyl) ether, bis(4-cyanate-3-iso-propylphenyl) ether, bis(4-cyanate-3,5-dimethylphenyl) ether, bis(2-cyanate-3-t-butyl-5-methylphenyl) ether, bis(4-cyanatephenyl)carbonyl, bis(4-cyanate-3-methylphenyl)carbonyl, bis(4-cyanate-3-t-butylphenyl) sulfide, bis(4-cyanate-3-iso-propylphenyl) carbonyl, bis(4-cyanate-3,5-dimethylphenyl)carbonyl, bis(2-cyanate-3-t-butyl-5-methylphenyl)carbonyl and the like. Among them, bis(4-cyanatephenyl)methane, bis(4-cyanate-3,5-dimethylphenyl)methane, 2,2-bis(4-cyanatephenyl) propane and 2,2-bis(4-cyanate-3,5-dimethylphenyl)propane are preferable, and 2,2-bis(4-cyanatephenyl)propane represented by the general formula (2) is more preferable.

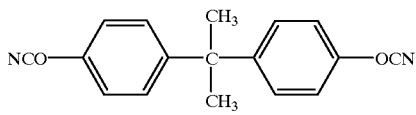

(2)

The cyanate crude product solution which comprises a cyanate represented by the general formula (1), a non-alcoholic solvent, and an unsubstituted phenol is obtained by reacting a phenol represented by the above-described general formula (1) with a cyanogen halide in a non-alcoholic solvent immiscible with water using a tertiary amine.

The unsubstituted phenol usually includes a raw material phenol and a phenol compound having an unsubstituted phenolic hydroxy group such as a mono-cyanated phenol, remaining in the cyanate crude product solution. The content of the unsubstituted phenol in the crude production solution is not particularly restricted, and usually 10% by weight or less, preferably from 0.5 to 5% by weight. When the content of the unsubstituted phenol in a cyanate crude product solution is in the range as described above, the cyanate crude product solution can be subjected in the step of contacting with a specific poor solvent. However, it is also permissible that the crude product solution is concentrated or diluted by adding a good solvent to appropriately adjust the content of the unsubstituted phenol in the crude product solution before contacting with a specific poor solvent.

The above-described good solvent is not particularly restricted providing it is an organic solvent which dissolves the cyanate represented by the general formula (1) and the unsubstituted phenol, and examples thereof include: halogenated hydrocarbons such as methylene chloride, chloroform and trichloroethane; ethers such as dimethylether, diethylehther and tetrahydrofuran; aromatic hydrocarbons such as benzene, xylene and chlorobenzene; and ketones such as 2-butanone, 3-pentanone, methylisobutylketone, 2-hexanone and cyclohexanone. Among them, tetrahydrofuran, toluene, methyl ethyl ketone, acetone or mixtures thereof is preferable.

It is preferable to add a good solvent in an amount required so that the content of the good solvent is from 10 to 400 parts by weight based on 100 parts by weight of the total amount of a cyanate represented by the general formula (1) and unsubstituted phenol in acrude product solution. For further improvement of isolation yield, the amount of a good solvent can be appropriately determined so that the content of the good solvent in a crude product solution is in the range from 10 to 30 parts by weight based on the above-described total amount, though it is not limited to this range.

When a cyanate crude product solution is contacted with a poor solvent described later, if other impurities are contained which are not dissolved even when the crude product solution is heated to 50° C., it is preferable to remove a filtrated residue previously by filtration and the like.

The poor solvent contains an alcohol and water. Preferably used are the alcohols which have a boiling point below 100° C., or a azeotropic point of its water mixture below 100° C. Examples of the alcohols include, but not limited to, methanol, ethanol, 1-propanol, 2-propanol, 1-butanol, 2-butanol, 2-methyl-1-propanol, 2-methyl-2-propanol, cyclohexanol, and mixtures thereof. Having less reactivity with a cyanate, secondary or tertiary alcohols such as 2-propanol, 2-butanol and 2-methyl-2-propanol are preferable, and 2-propanol (isopropyl alcohol) is especially preferable.

The amount of water in a poor solvent is usually from 10 to 100 parts by weight based on 100 parts by weight of alcohols, and for purification of a cyanate with increased isolation yield, it is preferably from 15 to 30 parts by weight.

Regarding this poor solvent, an alcohol may be previously mixed with water and allowed to contact with the above-described crude product solution, or they may be added separately to the above-described crude product solution to be in contact each other.

The amount of a poor solvent when this poor solvent is allowed to contact with a crude product solution is not particularly restricted, and usually, it is preferably from 50 to 300 parts by weight, more preferably from 100 to 200 parts by weight, based on 100 parts of the crude product solution.

In the purification method of the present invention, when the above-described poor solvent is allowed to contact with the above-describe crude product solution to crystallize the cyanate, the temperature for crystallization of the cyanate is preferably from −20° C. to 40° C. for avoiding reaction of the cyanate with the alcohol. For further increasing isolation yield, it is desirably from −20° C. to 10° C.

In the purification method of the present invention, a desired cyanate can be obtained efficiently and at high purity by performing known washing, drying under reduced pressure and the like on the above-described crystallized or precipitated purified product.

The filtrate discharged in the crystallization procedure comprises a cyanate and an unreacted phenol (raw material phenol, mono-cyanate, etc.), an alcohol and a non-alcoholic solvent, and usually, the filtrate forms an uniform solution.

The present invention also provides the separation method of alcohol and non-alcoholic solvent in the filtrate.

The ratio of alcohol to a non-alcoholic solvent in a filtrate discharged in the crystallization step is controlled to a specific ratio, and the water content in the filtrate is adjusted to a specific content, then the filtrate is separated into an oil layer and an aqueous layer. The alcohol and water contained in the aqueous layer can be separated from the non-alcoholic solvent by rectification.

In the above separation step, the weight ratio of alcohol to non-alcoholic solvent in a filtrate (alcohol/non-alcohol solvent) is controlled to from 20/80 to 90/10. In addition, it is necessary that water content in the filtrate is controlled to from 80 to 180 parts by weight based on 100 parts by weight of the total amount of alcohol and a non-alcoholic solvent contained in the filtrate. When the ratio of alcohol/non-alcohol solvent or the water content is out of the above-described ranges, the filtrate can not be separated into an aqueous layer and an oil layer. When the water content ratio is outside the upper limit of the above-described ratio, the amount of discharged water increases undesirably.

Methods for controlling the ratio of alcohol to non-alcoholic solvent and the water content are not particularly restricted, and for example, the amount of a non-alcoholic solvent, the added amount of a poor solvent, and the ratio of alcohol to non-alcoholic solvent can be previously controlled within the above-described ranges, with removal of a non-alcoholic solvent by partial concentration, and also, controlled by addition of deficient amount of alcohol. on the other hand, for control of water content, deficient amount of water may simply be added. Water-containing alcohol may be used for such control, and the adding amount of the water-containing alcohol can be determined by regarding the water content in alcohol as water. As such a water-containing alcohol, there can be utilized, for example, an alcohol washed filtrate containing water, alcohol and non-alcoholic solvent obtained by rinse treatment with alcohol or alcohol-containing aqueous solution for purification of a cyanate crystallized, and further, a water washed solution containing water and alcohol obtained by washing with water after the above-described rinse treatment.

The controlling the amounts of alcohol, water and the like, is preferably carried out at such lower temperature that a non-alcoholic solvent is not extracted into an aqueous layer, and specifically, it is conducted at a temperature usually from 0 to 60° C., preferably from 0 to 30° C.

An oil layer obtained by the above-described separation contains most of impurities composed of compounds containing an unsubstituted phenol migrated, and contains substantially no water, therefore, this oil layer can be burned out.

In the separation method of the present invention, alcohol can be separated by rectifying an aqueous layer essentially consisting of alcohol, water and non-alcoholic solvent. The aqueous layer sometimes further contains a small amount of a cyanate and impurities such as hydrolyzed product thereof and the like.

By rectification, the aqueous layer can be distilled off at an azeotropic mixture of alcohol/water. When stage number of rectification is higher and reflux ratio is higher, separation efficiency is higher. Specifically, rectification conditions can be appropriately determined by gas-liquid equilibrium of an aqueous layer-containing solution according to a known method (e.g., Theory and Calculation of Chemical Machine, chapter 7, Distillation, Section 5, Distillation Apparatus, Kamei edit., Sangyo Tosho (1982)).

An alcoholic aqueous solution obtained by rectification scarcely contains non-alcoholic solvent, and can be recycled as a poor solvent for crystallization.

EXAMPLE

The following examples further illustrate the present invention in detail, but do not limit the present invention.

Measurement by liquid chromatography:
Moving phase: water (liquid A) and acetonitrile (liquid B) under gradient solution condition.
Inner standard: 2-ethylhexyl benzoate
Detection: wavelength of UV 254 nm.
Measurement by Gas chromatography
Carrier gas: He
Absolute calibration line method using a sample dissolved at a certain concentration in acetone
Detector: FID

Synthesis Example

In a 3 L glass vessel equipped with a thermometer and an introducing tube extending to below the surface of raw material liquid, 1 L of 2-propanol was cooled to 0 to 5° C., then, to this was added 136 g of cyanogen chloride. Then, a previously cooled solution comprising 228 g of 2,2-bis(p-hydroxyphenyl)propane and 210 g of triethylamine per 1 L of 2-propanol was introduced with stirring over 1 hour through a measuring pump and they were allowed to react. In completion of the reaction, a crystalline sludge was separated from 2-propanol by filtration under suction. The filtered residue was washed completely with water, and dried in air at 35° C. to obtain a crude product of a cyanate.

The resulted crude product was analyzed by liquid chromatography (LC) to find it was a 95% by weight 2,2'-bis(4-cyanatephenyl)propane crude product containing 5% by weight of a monocyanate substitution product of bisphenol A.

Example 1

67 g of toluene was added and mixed with 200 g of the crude product obtained in the synthesis example to prepare a 2,2'-bis(4-cyanatephenyl)propane crude product solution. 325 g of a 2-propanol poor solvent containing 15% by weight of water was added and mixed with the resulted crude product solution, and the mixture was cooled to 5° C. over 2 hours, and crystallized solid was taken out. The resulted solid was washed with 325 g of a 2-propanol poor solvent containing 15% by weight of water, then, washed with 325 g of water, and further dried under a reduced pressure of 50 torr at 60° C., to obtain 171 g of 2,2'-bis(4-cyanatephenyl)propane. When the resulted 2,2'-bis(4-cyanatephenyl)propane was analyzed by LC to find that the purity was 99.5%, the isolation yield was 90%, the phenol content (content of 2,2'-bis(4-hydroxyphenyl)propane and 2-(4-cyanatephenyl)-2'-bis(4-hydroxyphenyl)propane) was 0.1%, and the content of volatile components was less than 0.01%.

Examples 2 to 4 and Comparative Examples 1 and 2

Purification was conducted as in Example 1 except that a crude product solution and a poor solvent shown in Table 1 were used. The isolation yield, purity, phenol content and volatile component content of the resulted purified product were measured. The results are shown in Table 1.

Abbreviations in Table 1 are as described below.
BPA-C: 2,2'-bis(4-cyanatephenyl)propane
Unsubstituted phenol: mixture of 2,2'-bis(4-hydroxyphenyl)propane and 2-(4-cyanatephenyl)-2'-(4-hydroxyphenyl)propane
TEN: toluene (manufactured by Mitsubishi Chemical Co., Ltd.)
MIBK: methyl isobutyl ketone (manufactured by Wako Pure Chemical Industries Ltd., guaranteed reagent)
THF: tetrahydrofuran (manufactured by Wako Pure Chemical Industries Ltd., guaranteed reagent)
N. D.: not detected by liquid chromatography

TABLE 1

|  |  | Comparative example 1 | Comparative example 2 | Example 2 | Example 3 | Example 4 |
|---|---|---|---|---|---|---|
| Crude product solution of cyanate | Amount of crude product solution | 1000 g | 333 g | 266 g | 666 g | 250 g |
| | Content of BPA-C | 19.4% | 60% | 75% | 30% | 80% |
| | Content of unsubstituted phenol | 1.0% | 3.2% | 3.9% | 1.5% | 4.2% |
| | Kind of good solvent | TEN | MIBK | THF | TEN | MIBK |
| | Content of good solvent | 79.6% | 36.8% | 21.1% | 68.5% | 15.8% |
| Poor solvent | Kind of organic solvent | hexane | 2-propanol | 2-propanol | 2-propanol | 2-propanol |
| | Content of organic solvent | 400 g | 325 g | 276 g | 276 g | 276 g |
| | Content of water | — | — | 48 g | 48 g | 48 g |
| Crystallization temperature | | 23° C. | 5° C. | 5° C. | 5° C. | 5° C. |
| Results | Isolation yield | 99.8% | 79% | 89% | 85% | 93% |
| | Purity | 95.0% | 97.0% | 99.8% | 99.9% | 99.7% |
| | Content of unsubstituted phenol | 5% | 2.4% | 0.1% | N.D. | 0.1% |
| | Content of volatile component | <0.01% | <0.01% | <0.01% | <0.01% | <0.01% |

As is known from results in Table 1, in Comparative Example 1, impurity phenol preferentially deposited and a cyanate could not be obtained at high purity since hexane was used as a poor solvent. In Example 2, the isolation yield of a cyanate was lower and phenol removing effect is smaller as compared with the examples since only 2-propanol was used as a poor solvent.

Example 5

<Synthesis of cyanate and cyanate-containing crude product solution>

In a beaker, 255.0 g of 2,2'-bis(4-hydroxypheny)propane (hereinafter, abbreviated as BPA)(manufactured by Mitsui Chemical Co., Ltd.), 248.7 g of triethylamine (manufactured by Daicel Chemical Industries Ltd.) and 255.0 g of toluene (manufactured by Mitsubishi Chemical Co., Ltd.) were mixed and dissolved to prepare a BPA-containing solution while absence of impurities was confirmed visually.

A flask charged with 127 ml of cyanogen chloride and 340 g of toluene was installed into a reaction vessel equipped with a Pfaudler blade and the thermometer and cooled. Into this flask was added dropwise the BPA-containing solution prepared above over about 2 hours while controlling the temperature of the solution in the flask to 10° C. or less. After the addition, the solution was stirred for 30 minutes at a temperature of 10° C. or less to produce (2,2'-bis(4-cyanatephenyl)propane).

The reaction solution was washed with 595 g of water, 3 times at 40° C., to obtain a cyanate-containing crude product solution. The resulted crude product solution was analyzed by liquid chromatography. As a result, the yield of 2,2'-bis(4-cyanatephenyl)propane was 96.1%, the yield of 2-(4-cyanatephenyl)-2'-(4-hydroxyphenyl)propane was 0.6%, and the yield of 2,2'-bis(4-hydroxyphenyl)propane was 0.2%.

Then, the resulted cyanate-containing crude product solution was concentrated under reduced pressured until the toluene content reached to 26% by weight, then, 510 g of a poor solvent of isopropyl alcohol/water=85/15 (by weight) was added, and the mixture was immediately cooled and stirred. After cooling to an inner temperature of 3° C., filtration was conducted to obtain a white crystal and an original filtrate. To the white crystal, 510 g of isopropyl alcohol/water=85/15 (by weight) was further added, and the mixture was rinsed (this rinsed filtrate is referred to as "alcohol washed filtrate"), subsequently, substituted with510 g of cold water (this water substituted filtrate is referred to as "water washed filtrate"), to obtain a cake. The resulted cake was dried under reduced pressure to obtain a white crystal, and this was analyzed by liquid chromatography. As a result, 286.0 g (yield 92%) of 2,2'-bis(4-cyanatephenyl)propane was obtained, and 2-(4-cyanatephenyl)-2'-(4-hydroxyphenyl)propane, 2,2'-bis(4-hydroxyphenyl)propane and other phenol components were not detected.

Further, regarding the above-described original filtrate, alcohol washed solution and water washed solution, the contents of nonvolatile components, toluene, isopropyl alcohol and water were analyzed. The analysis results are shown in Table 2. Regarding analysis of nonvolatile components, a cyanate and other impurities were dried for 3 hours in a draft oven (105° C.). Toluene and isopropyl alcohol were analyzed by gas chromatography. Water content was calculated as remainder of the above-described three components.

TABLE 2

|  | Original filtrate | Alcohol washed filtrate | Water washed filtrate |
|---|---|---|---|
| Weight of filtrate (g) | 630 | 487 | 525 |
| Composition |  |  |  |
| Nonvolatile component (%) | 8 | 0 | 0 |
| Toluene (%) | 17 | 1 | 0 |
| Isopropyl alcohol (%) | 64 | 85 | 8 |
| Water (%) | 11 | 14 | 92 |

<Separation of filtrate and separation of alcohol>

The total amount of the original filtrate and water washed filtrate shown in Table 2 was charged, and stirred at 20° C. to be separated into 230 g of an oil layer and 924 g of an aqueous layer. In this procedure, toluene/isopropyl alcohol=19/81 (by weight), and the water content based on 100 parts of the total amount of toluene and alcohol was 100 parts by weight.

The resulted oil layer was composed of 20% by weight of toluene, 37% by weight of isopropyl alcohol, and 2% by weight of nonvolatile components containing 2,2'-bis(4- cyanatephenyl)propane, 2-(4-cyanatephenyl)-2'-(4-hydroxyphenyl)propane and 2,2'-bis(4-hydroxyphenyl)propane, and could be burned.

The aqueous layer was charged in a round bottomed flask together with the alcohol washed filtrate shown in Table 2, and rectified at a reflux ratio of 8 under normal pressure using a rectification apparatus equipped with a rectification column (corresponding to stage number of 20) having a diameter of 30 mm and a height of 700 mm filled with a dickson having a diameter of 3 mm and a height of 3 mm. As a result, 180 g of a toluene-containing solution was distilled until the bottom temperature reached 82° C., and then, 676 g of a 85% by weight isopropyl alcohol aqueous solution (recovering ratio as alcohol: 78%) was obtained until the bottom temperature reached 100° C. This alcohol contained only 0.3% by weight of toluene. The remaining bottom remainder was filtrated through filter paper to result a clear aqueous solution.

Example 6

<Synthesis of cyanate and cyanate-containing crude product solution>

A cyanate-containing crude product solution was obtained in the same manner as in Example 5 except that methyl isobutyl ketone was used instead of toluene used in Example 5. The resulted crude product solution was analyzed by liquid chromatography. As a result, the yield of 2,2'-bis(4-cyanatephenyl)propane in this solution was 98.0%, the yield of 2-(4-cyanatephenyl)-2'-(4-hydroxyphenyl)propane was 0.3%, and 2,2'-bis(4-hydroxyphenyl)propane was not recovered.

This crude product solution was concentrated under reduced pressured until the methyl isobutyl ketone content reached to 25% by weight, then, 510 g of a poor solvent of isopropyl alcohol/water=85/15 (by weight) was added, and the mixture was immediately cooled and stirred. Then, after cooling to an inner temperature of 3° C., filtration was conducted to obtain a white crystal and a liquid concentrate. To the white crystal, 510 g of isopropyl alcohol/water=85/15 (by weight) was further added, and the mixture was rinsed (this rinsed filtrate is referred to as "alcohol washed filtrate"), subsequently, substituted with 510 g of cold water (this water substituted filtrate is referred to as "water washed filtrate"), to obtain a cake. The resulted cake was dried under reduced pressure to obtain a white crystal of 279.8 g (yield 90%) of 2,2'-bis(4-cyanatephenyl)propane, and this was analyzed by liquid chromatography. As a result, 2-(4-cyanatephenyl)-2'-(4-hydroxyphenyl)propane, 2,2'-bis(4-hydroxyphenyl)propane and other phenol components were not detected. Further, the original filtrate, alcohol washed solution and water washed solution were subjected to the same analysis as in Example 5. The analysis results are shown in Table 3. In this example, the methyl isobutyl ketone content was analyzed instead of the toluene content in Example 5.

TABLE 3

|  | Original filtrate | Alcohol washed filtrate | Water washed filtrate |
|---|---|---|---|
| Weight of filtrate (g) | 628 | 490 | 524 |
| Composition |  |  |  |
| Nonvolatile component (%) | 7 | 0 | 0 |
| Methyl isobutyl ketone (%) | 17 | 2 | 0 |
| Isopropyl alcohol (%) | 64 | 84 | 10 |
| Water (%) | 12 | 14 | 90 |

<Separation of filtrate and separation of alcohol>

The total amount of the original filtrate and water washed filtrate shown in Table 3 was charged, and stirred at 20° C. to be separated into 185 g of an oil layer and 967 g of an aqueous layer. In this procedure, methyl isobutyl ketone/isopropyl alcohol=19/81 (by weight), and the water content based on 100 parts of the total amount of methyl isobutyl ketone and alcohol was 96 parts by weight.

The resulted oil layer was composed of 15% by weight of methyl isobutyl ketone, 42% by weight of isopropyl alcohol, and 2% by weight of nonvolatile components containing 2,2'-bis(4-cyanatephenyl)propane, 2-(4-cyanatephenyl)-2'-(4-hydroxyphenyl)propane and 2,2'-bis(4-hydroxyphenyl)propane, and could be burned.

The aqueous layer was charged in a round bottomed flask together with the alcohol washed filtrate shown in Table 3, and rectified under the same conditions as in Example 5, and as a result, 650 g of a 85% by weight isopropyl alcohol aqueous solution (recovering ratio as alcohol: 75%) was obtained until the bottom temperature reached 85° C. This alcohol contained only 1.5% by weight of methyl isobutyl ketone.

Example 7

A cyanate-containing crude product solution was obtained in the same manner as in Example 5, then, a original filtrate, alcohol washed filtrate, water washed filtrate and 290.6 g of a white crystal were obtained in the same manner as in Example 5 except that 100% isopropyl alcohol was used instead of isopropyl alcohol/water=85/15 (by weight) in Example 5. This white crystal was analyzed by liquid chromatography. As a result, the yield of $2,2^1$-bis(4-cyanatephenyl)propane was 92%, the yield of 2-(4-cyanatephenyl)-2'-(4-hydroxyphenyl)propane was 1.0%, and the yield of 2,2'-bis(4-hydroxyphenyl)propane was 0.5%. Other phenol components were not detected. Further, the original filtrate, alcohol washed solution and water washed solution were subjected to the same analysis as in Example 5. The results are shown in Table 4.

TABLE 4

|  | Original filtrate | Alcohol washed filtrate | Water washed filtrate |
|---|---|---|---|
| Weight of filtrate (g) | 731 | 510 | 510 |
| Composition |  |  |  |
| Nonvolatile component (%) | 8 | 0 | 0 |
| Toluene (%) | 29 | 1 | 0 |
| Isopropyl alcohol (%) | 63 | 99 | 13.5 |
| Water (%) | 0 | 0 | 86.5 |

<Separation of filtrate and separation of alcohol>

The total amount of the original filtrate and water washed filtrate shown in Table 4 was charged and 300 g of water was additionally added, and stirred at 20° C. to be separated into 230 g of an oil layer and 1311 g of an aqueous layer. In this procedure, toluene/isopropyl alcohol=29/71 (by weight), and the water content based on 100 parts of the total amount of toluene and alcohol was 100 parts by weight.

The aqueous layer was charged in a round bottomed flask together with the alcohol washed filtrate shown in Table 4, and rectified under the same conditions as in Example 5, and as a result, 180 g of a toluene-containing solution was distilled until the bottom temperature reached 82° C., subsequently, 949 g of a 85% by weight isopropyl alcohol aqueous solution (recovering ratio as alcohol: 78%) was distilled until the bottom temperature reached 100° C. This alcohol contained only 0.3% by weight of toluene.

Comparative Example 3

The original filtrate, alcohol washed filtrate and water washed filtrate in Example 5 were so used that toluene/ isopropyl alcohol was 11/89 (by weight) and the water content based on 100 parts of the total amount of toluene and alcohol was 64 parts by weight. The resulted solution was stirred at 20° C. to find no separation. The resulted solution was rectified under the same conditions as in Example 5, and as a result, 570 g of a toluene-containing waste liquid was distilled until the bottom temperature reached 82° C., subsequently, 589 g of a 85% by weight isopropyl alcohol aqueous solution (recovering ratio as alcohol: 68%) was distilled until the bottom temperature reached 100° C. The solution in the column was opaque, and tar was adhered to the concentrated bottom and wall. The adhered tar was analyzed by liquid chromatography to find a peak of the reaction product of the cyanate and alcohol and other may peaks.

According the purification method of the present invention, a cyanate having high purity can be obtained at high yield since the method includes a step in which a specific cyanate crude product solution is allowed to contact with a poor solvent containing an alcohol and water to crystallize or precipitate a cyanate. Further, in the present invention, ignition crisis is very low and purification of a cyanate is possible very safely and in industrial scale, since not only alcohols but also water are contained as poor solvents.

What is claimed is:

1. A method for purifying a cyanate wherein a cyanate crude product solution comprising a cyanate represented by the general formula (1), an unsubstituted phenol and non-alcoholic solvent is allowed to contact with a poor solvent containing an alcohol and water, to crystallize or precipitate said cyanate:

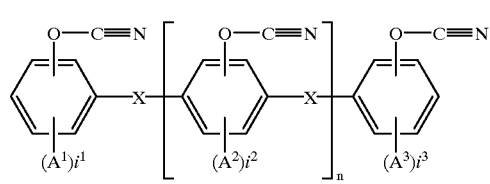

in the formula (1), $A^1$ to $A^3$ each independently represents a hydrogen atom or an alkyl group having 1 to 6 carbon atoms; X represents a single bond, an organic group having 1 to 20 carbon atoms, a carbonyl group, a sulfone group, a divalent sulfur atom or oxygen atom; n represents an integer of 0 to 3; and $i^1$ to $i^3$ each independently represents an integer of 0 to 4.

2. The method according to claim 1, wherein when said crude product solution is allowed to contact with said poor solvent, the content of the unsubstituted phenol in the crude product solution is 10% by weight or less and the content of water in the poor solvent is from 10 to 100 parts by weight based on 100 parts by weight of the alcohol.

3. The method according to claim 1 or 2, wherein the crude product solution contains a good solvent which dissolves the cyanate and the unsubstituted phenol.

4. The method according to claim 3, wherein the good solvent is a ketone, an aromatic hydrocarbon, a halogenated hydrocarbon, or a mixture thereof.

5. The method according to claim 3, wherein the good solvent is selected from the group consisting of toluene, tetrahydrofuran, methyl ethyl ketone, methyl isobutyl ketone, acetone and mixtures thereof.

6. The method according to claim 1, wherein the cyanate is 2,2-bis(4-cyanatephenyl)propane represented by the formula (2):

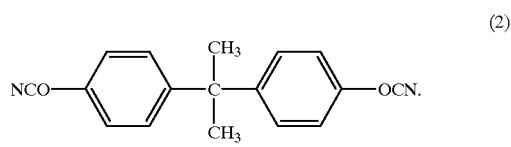

7. The method according to claim 1, wherein the alcohol is a secondary or tertiary alcohol.

8. The method according to claim 1, wherein the alcohol is 2-propanol.

9. A method for separating an alcohol comprising the steps of:

(1) adjusting the ratio of the alcohol to the non-alcoholic solvent (alcohol/non-alcoholic solvent) in the filtrate discharged in the crystallization or precipitation process of claim 1 to from 20/80 to 90/10 and the water content to from 80 to 180 parts by weight based on 100 parts by weight of the total amount of the alcohol and the non-alcoholic solvent contained in the filtrate, (2) separating the filtrate into an oil layer and an aqueous layer and (3) rectifying the aqueous layer which essentially consists of an alcohol, non-alcoholic solvent and water, to separate the alcohol and water in the aqueous layer from the non-alcoholic solvent.

* * * * *